United States Patent [19]

Horrobin

[11] Patent Number: 4,977,187

[45] Date of Patent: Dec. 11, 1990

[54] TREATING SCHIZOPHRENIA WITH ESSENTIAL FATTY ACID COMPOSITIONS

[75] Inventor: David F. Horrobin, Guildford, England

[73] Assignee: Efamol Holdings PLC, Guildford, England

[21] Appl. No.: 359,565

[22] Filed: Jun. 1, 1989

[30] Foreign Application Priority Data

Jun. 10, 1988 [GB] United Kingdom ............... 8813766

[51] Int. Cl.$^5$ ............................................ A61K 31/20
[52] U.S. Cl. ................................................... 514/560
[58] Field of Search ......................................... 514/560

[56] References Cited

U.S. PATENT DOCUMENTS 4,273,763  6/1981  Harrobin ............................. 514/560
4,302,447  11/1981  Harrobin ............................ 514/560

FOREIGN PATENT DOCUMENTS 0115419  8/1984  European Pat. Off. .
0234733  9/1987  European Pat. Off. .
0296751  12/1988  European Pat. Off. .
3719097  6/1988  Fed. Rep. of Germany .
2148713  6/1985  United Kingdom .

*Primary Examiner*—Stanley J. Friedman
*Attorney, Agent, or Firm*—Nixon & Vanderhye

[57] ABSTRACT

Method of, and preparations of medicaments for, treating schizophrenia and/or associated tardive dyskinesia by combining an essential fatty acid selected from GLA and higher N-6 series acids with an essential fatty acid selected from stearidonic acid and higher n-3 series acids in effective daily amounts of 10 mg and 50 g of each acid.

2 Claims, No Drawings

TREATING SCHIZOPHRENIA WITH ESSENTIAL FATTY ACID COMPOSITIONS

The invention relates to essential fatty acid (EFA) compositions and treatments therewith.

GENERAL DISCUSSION

The bodily EFAs, falling largely into the two series known as the n-6 and n-3 EFAs of structure and relation as follows, and sharing, it is believed, common enzymes in the two pathways, are:

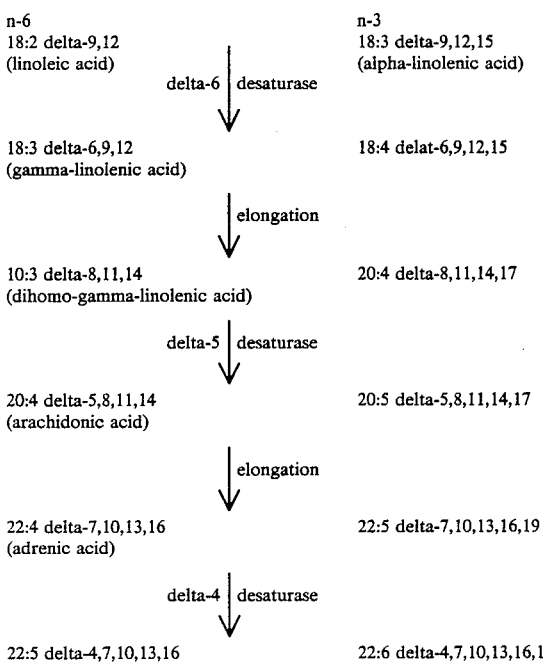

| n-6 | n-3 |
|---|---|
| 18:2 delta-9,12 (linoleic acid) | 18:3 delta-9,12,15 (alpha-linolenic acid) |
| 18:3 delta-6,9,12 (gamma-linolenic acid) | 18:4 delat-6,9,12,15 |
| 10:3 delta-8,11,14 (dihomo-gamma-linolenic acid) | 20:4 delta-8,11,14,17 |
| 20:4 delta-5,8,11,14 (arachidonic acid) | 20:5 delta-5,8,11,14,17 |
| 22:4 delta-7,10,13,16 (adrenic acid) | 22:5 delta-7,10,13,16,19 |
| 22:5 delta-4,7,10,13,16 | 22:6 delta-4,7,10,13,16,19 |

The acids are in the natural all-cis configuration. In the n-6 series, commonly used names are as follows: for the 18:2 and 18:3 (octadeca di- and trienoic) acids linoleic acid and gamma-linolenic acid (GLA); for the 20:3 and 20:4 (eicosatri- and tetraenoic) acids dihomo-gamma-linolenic acid (DGLA) and arachidonic acid (AA); and for the 22:4 (docosa-tetraenoic) acid adrenic acid. In the n-3 series only alpha-linolenic acid (18:3) is commonly referred to by a non-systematic name but the name stearidonic acid does exist for the 18:4 n-3 acid. Initials are also used e.g. EPA for the 20:5 (eicosapentaenoic) acid.

BACKGROUND OF THE INVENTION

The brain is exceptionally rich in EFAs which make up over 20% of its dry weight and disorders in EFA metabolism may be expected to be reflected in mental disorders. We have previously discussed, for example in EP-A-0003407, a relation of schizophrenia to a deficit of 1-series prostaglandins (PGs) derived from dihomo-gamma-linolenic acid (DGLA). DGLA can be formed in the body from dietary linoleic acid via gamma-linolenic acid (GLA). Since the conversion of dietary linoleic acid to GLA may be restricted by a variety of factors we proposed that schizophrenia may be treated by GLA or DGLA alone or in combination with a variety of factors which may enhance the formation of 1-series PGs.

It has also been proposed that vitamin E may improve tardive dyskinesia (TD) on the grounds that anti-schizophrenic drugs may damage nerve endings by generating free radicals. Large doses of vitamin E, in excess of 400 IU per day, have been shown to improve the condition (Lohr J. B., Cadet, J. L., Lohr, M. A., "Alpha-Tocopherol in Tardive Dyskinesia" Lancet 1:913-4, 1987).

EXPERIMENTAL WORK

We have recently carried out a substantial investigation of the levels of EFAs in plasma and red cell phospholipids of schizophrenics and of the effects of treatment with GLA in the form of evening primrose oil. In the biochemical investigation some of the schizophrenics were free of TD while some suffered from it. The condition is a disorder of movement control in which a variety of abnormal and involuntary movements takes place. It sometimes occurs in schizophrenics who have never been treated with modern anti-schizophrenic drugs, but it is considerably more common in those who have been treated with such drugs, notably those which have the ability to block dopamine receptor function.

In schizophrenics with and without TD we have found that in both plasma and red cell phospholipids the levels of n-6 EFAs are substantially reduced. In plasma the levels of n-3 EFAs are moderately elevated, whereas they are reduced in the red cell membranes. With regard to schizophrenic illness, the red cell abnormalities may be more important since it is cell membranes in the brain which are rich in EFAs. A problem of incorporation of EFAs into red cell membranes may reflect problems of incorporation into brain membranes. Consistently, in our study, the EFA abnormalities in schizophrenics with TD were substantially greater than in schizophrenics without TD (Table 1):

| FATTY ACID | NORMAL | S − TD | S + TD |
|---|---|---|---|
| Linoleic | 14.0 | 12.3$^x$ | 9.2$^{xx}$ |
| DGLA | 1.6 | 1.2$^x$ | 0.6$^{xx}$ |
| AA | 17.2 | 12.1$^{xx}$ | 8.1$^{xx}$ |
| EPA | 1.4 | 1.1$^x$ | 0.6$^{xx}$ |
| DHA | 6.2 | 4.8$^x$ | 3.1$^{xx}$ |

In a double-blind, placebo-controlled trial, evening primrose oil or placebo were given to schizophrenics with TD. Half of the patients were put on placebo for four months and then switched to evening primrose oil for a further four months and the other half were treated in the reverse sequence. Patients were scored with regard to TD and to psychiatric status at the baseline and throughout the trial. Scores for TD (Abnormal Involuntary Movement Scale, of Simpson) and for psychosis (Comprehensive Psychopharmacological Rating Scale (CPRS)) are shown in Table 2:

TABLE 2

Responses to active and placebo treatment on the Simpson TD scale and the CPRS psychosis scale

| | Active | Placebo |
|---|---|---|
| Change in Simpson score | −3.8 | −3.0$^x$ |
| Change in CPRS score | −5.1 | +1.3$^{xx}$ |

*Two groups different at p < 0.05 (x) p < 0.01 (xx).

Evening primrose oil was modestly better than placebo in improving the Simpson score and highly significantly better in improving the psychosis score.

THE INVENTION

We have considered these matters and it has occurred to us that one of the actions of free radicals is to damage polyunsaturated fatty acids, which are very easily oxidised. We believe that free radical damage to polyunsaturated fatty acids is involved in the reduction in EFAs which we have demonstrated occurs in schizophrenics, especially those with TD. EFAs will therefore, and this is the basis of the major aspect of the present invention, have synergistic actions with high doses of vitamin E. The vitamin E alone will inhibit ongoing free radical damage but will not restore the already depleted EFAs. Provision of EFAs with the vitamin E will restore the depleted levels of EFAs, with a specific and synergistic action between EFAs and vitamin E.

The effect of vitamin E in inhibiting EFA peroxidation has been known for many years but to our knowledge no one has ever proposed that very high levels of vitamin E should be used in therapy in conjunction with EFAs and certainly no one has proposed that very high levels of vitamin E should be used with essential fatty acids in treatment of schizophrenia. We therefore here propose that combinations of high levels of vitamin E and EFAs have general utility in the treatment of a variety of diseases in which free radicals are known to play a part or in which either vitamin E or EFAs have already been shown to be therapeutically effective. Free radicals are believed to play a key role in all disorders of inflammation, in alcoholism and, now, in complications of schizophrenia. EFAs have been shown to have therapeutic effects in reversing liver and brain damage due to high alcohol consumption, in a wide variety of human and animal examples of inflammation e.g. atopic eczema, rheumatoid arthritis, experimental allergic encephalomyelitis (the animal model of multiple sclerosis), adjuvant arthritis, glomerulonephritis, urticaria, Sjogren's syndrome, Crohn's disease, irritable bowel syndrome, cystic fibrosis, psoriasis; in premenstrual syndrome; and in the complications of diabetes.

The most important polyunsaturated fatty acids in cell membranes appear to be DGLA and arachidonic acid (AA) of the n-6 series and EPA (20:5 n-3), 22:5 n-3 and DHA (22:6 n-3) of the n-3 series. Although linoleic acid is the main dietary precursor of the n-6 series and alpha-linolenic acid is the main dietary precursor of the n-3 series, in adult humans these fatty acids are not readily converted to their metabolites. Moreover, this conversion can be blocked by factors which are common, such as high cholesterol levels, diabetes, high alcohol intake or the presence of large amounts of trans fatty acids in the diet. There is therefore a preference for raising n-6 EFA levels by the administration of GLA and/or its metabolites and n-3 EFA levels by the administration of stearidonic acid (18:4 n-3) and/or its metabolites both of which by-pass the potentially impaired 6-desaturase step.

COMPOSITION

The compositions used in the invention and possibly to be the subject of divisional application in their own right, are most broadly of essential fatty acids selected from GLA and higher n-6 series acids and stearidonic acid and higher n-3 series acids, and vitamin E in an amount of 3% by weight or more based on the amount of said acids. The GLA and stearidonic acid are the most desirable as they are both generally available and readily convertible in the body to the higher acids of their series. Still more desirable is use of compositions containing both an n-6 acid preferably GLA and an n-3 acid preferably stearidonic acid. In all compositions, the amounts are suitably such as to provide conveniently for administration of EFAs 10 mg to 50 g per day, preferably 100 mg to 5 g/day. The amount of vitamin E administered is related to the amount of EFAs as noted above, 10 mg vitamin E being approximately 13.6 IU depending upon its source. Linoleic and/or alpha-linolenic acid may be used in the compositions as carriers for the other essential fatty acids.

Within the present claimed invention are:

(a) Methods of and preparations of medicaments for treating schizophrenia and/or associated tardive dyskinesia by combining an n-6 EFA selected as above desirably GLA, DGLA or AA, with an n-3 EFA selected as above desirably stearidonic acid, EPA, 22:5 n-3 or DHA. More than one EFA of each series may be present, but with or without vitamin E, based on our demonstration that red cell membranes in schizophrenics are deficient in both n-3 and n-6 EFAs. Desirably, the amounts of EFA and the optional vitamin E are as above.

(b) Composition for, methods of, and preparation of medicaments for treating skin disorders with an inflammatory component such as atopic eczema, psoriasis, acne, contact dermatitis or urticaria, which may be treated specifically with a topical preparation such as an ointment, cream or other form containing one or more EFAs as discussed above and vitamin E in which the amount of vitamin E is not less than 3% by weight of the total amount of EFAs present and the EFA or total EFA is preferably not less than 0.01% by weight of the composition, and up to 20% or 30%.

More generally, and possibly to be the subject of divisional applications in their own right, there are contemplated using or preparing the vitamin E containing compositions specified above, for treatment or prophylaxis of:

Schizophrenia, and other cerebral disorders including depression, alcoholism and senile and presenile dementias;

Liver, brain and other damage to the body caused by alcohol;

Premenstrual syndrome, dysmenorrhoea or other menstrual disorder;

Inflammatory disorders as referred to earlier herein in the second paragraph under the heading "The Invention"; and Complications due to diabetes mellitus such as retinopathy, neuropathy, nephropathy and cardiovascular disorders.

FORMS AND SOURCES OF EFAs

When derivatives of the EFAs are used as discussed below, the amounts are calculated as the EFA.

The EFAs can be and indeed normally will be used as an assimilable, pharmacologically acceptable and physiologically equivalent derivative and reference to EFAs herein (including in the claims) is to be taken as including reference to such derivatives. Identification of useful derivatives is by their having the valuable effect in the body of the acid itself, but conversion can be shown directly by gas chromatographic analysis of concentrations in blood, body fat, or other tissue by standard techniques, for example those of Pelick et al, p. 23, "Analysis of Lipids and Lipoproteins" Ed. Perkins, American Oil Chemists Society, Champaign, Illinois, U.S.A.

Convenient derivatives of EFAs include salts, amides, esters including glyceride esters and alkyl (e.g. $C_1$ to $C_4$) esters, and phospholipids.

Thus if desired, pharmaceutical compositions may be produced for use in the invention by associating the natural or synthetic acid, as such or as a derivative, with an acceptable pharmaceutical vehicle. It is, however, at present convenient to incorporate the acids into compositions in the form of available oils having a high content of the acids, hence references to "oils" herein.

Fish oils are a convenient source of n-3 EFAs, examples being fish body oils, especially of oily fish such as herring, mackerel, anchovies, pilchards, menhaden, tuna and salmon, fish gut oils, fish liver oils; oils derived from fermentation of certain fungi or culture of algae; oils from animals or birds consuming fish, such as seals.

At the present time known natural sources of oils having a high GLA acid content are few (there are no known natural sources of significant amounts of DGLA). One source of GLA currently available is the seed of Evening Primrose species such as *Oenothera biennis* L. and *Oenothera lamarckiana*, the oil extract therefrom containing GLA (about 8%) and linoleic acid (about 72%) in the form of their glycerides together with other glycerides (percentages based on total fatty acids). Other sources of GLA are Borage species such as *Borago officinalis* which, though current yield per acre is low, provide a richer source of gamma-linolenic acid than Oenothera oil. Recent studies on fungi which can be cultivated by fermentation promise a fungal oil source.

The oil is extracted from the seeds by one of the conventional methods of extraction such as cold pressure, screw pressure after partially cooking the seed or solvent extraction.

Fractionation of a typical sample of this oil in the form of methyl esters shows the relative proportions:

| | |
|---|---|
| Palmitate | 6.15 |
| Stearate | 1.6 |
| Oleate | 10.15 |
| Linoleate | 72.6 |
| Gamma-Linolenate | 8.9 |

The seed oil extracts referred to above can be used as such or can, for example, if desired, be fractionated to yield an oily composition containing the triglycerides of gamma-linolenic and linoleic as the main fatty acid components, the gamma-linolenic acid content being if desired a major proportion. Seed oil extracts appear to have a stabilising effect upon dihomo-gamma-linolenic acid if present.

For the n-6 series acids higher than GLA synthesis is possible though not simple, for example for DGLA, but the higher acids are commonly available in small quantities from slaughterhouses, for example adrenic acid from adrenal glands. Arachidonic acid is present in substantial amounts in meat, eggs, certain fish oils and cultures of certain micro-organisms.

VETERINARY APPLICATIONS

It will be understood that where a disorder of a kind calling for treatment in animals arises, the invention while described primarily in terms of human medicine and treatment is equally applicable in the veterinary field.

PACKS

If it is not desired to have compositions comprising different active materials together, packs may be prepared comprising the materials presented for separate, or part joint and part separate administration in the appropriate relative amounts, and use of such packs is within the purview of this invention.

DIETARY COMPOSITIONS

The invention is chiefly described in relation to methods of treatment and pharmaceutical compositions, but it will be understood that the EFAs and/or the vitamin E, being in the nature of dietary supplements, could be incorporated in a dietary margarine or other foodstuff.

PHARMACEUTICAL PRESENTATION

The compositions according to the invention are conveniently in a form suitable for oral, parenteral, etc. administration in a suitable pharmaceutical vehicle, as discussed in detail for example in Williams GB-A-1,082,624 to which reference may be made, and in any case very well known generally for any particular kind of preparation. Thus, for example, tablets, capsules, ingestible liquid or powder preparations can be prepared as required. Injectable solutions of hydrolysed Oenothera oil and fish oil may be prepared using albumin to solubilise the free acid.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

EXAMPLES

The following are specific examples of the invention, for use in treatment or prophylaxis in man against the conditions set out:

A. For Schizophrenia and Tardive Dyskinesia

1. Capsules containing 50% evening primrose oil (EPO) and 50% fish oil (containing 18% EPA and 12% DHA) for treatment of schizophrenia and/or associated tardive dyskinesia, 4 to 16 capsules of 500 mg total oil to be taken per day.

2. Capsules containing 200 mg purified GLA and 200 mg purified EPA for treatment of schizophrenia, 2 to 8 capsules to be taken per day.

B. For the Disorders Generally

3. Capsules containing 50% EPO and 50% fish oil total 500 mg together with 40 mg (approximately 50 IU) vitamin E to be taken 12 per day.

4. Capsules containing 300 mg of AA, 300 mg of DHA and 75 mg (approximately 100 IU) of vitamin E to be taken 2 to 10 per day.

5. Capsules containing 50 mg of GLA, 50 mg of DGLA, 50 mg of AA, 50 mg of stearidonic acid, 50 mg of EPA, 50 mg of DHA plus 40 mg (approximately 50 IU) of vitamin E to be taken 4 to 12 per day.

6. Formulations for parenteral or enteral administration containing EPO, fish oil and vitamin E for the administration at rates which will deliver more than 110 mg (approximately 150 IU) of vitamin E per day and the amounts of EPO and fish oil taken in Example 1.

C. For Skin Disorders

7. Preparations for topical administration in which the ratio of EFA to vitamin E is not more than 20:1 and comprising in each 100 g, 2 g of GLA, 1 g of EPA and 220 mg (approximately 300 IU) of vitamin E.

I claim:

1. A method of treating schizophrenia comprising administering to a patient in need of same an effective amount of a composition comprising an essential fatty acid selected from GLA and a higher n-6 series acid with an essential fatty acid selected from stearidonic acid and a higher n-3 series acid in effective daily amounts of 10 mg and 50 g of each acid, and vitamin E present in an amount at least of 3% by weight based on the total amount of said acids.

2. The method according to claim 1, wherein the n-6 EFA is selected from GLA, DGLA and AA and the n-3 EFA is selected from stearidonic acid, EPA, 22:5 n-3 and DHA.

* * * * *